(12) United States Patent
Farmer et al.

(10) Patent No.: US 11,412,740 B2
(45) Date of Patent: Aug. 16, 2022

(54) LARGE-SCALE AEROBIC SUBMERGED PRODUCTION OF FUNGI

(71) Applicant: Locus IP Company, LLC, Solon, OH (US)

(72) Inventors: Sean Farmer, North Miami Beach, FL (US); Ken Alibek, Solon, OH (US); Sharmistha Mazumder, Copley, OH (US); Tyler Dixon, Kent, OH (US)

(73) Assignee: LOCUS IP COMPANY, LLC, Solon, OH (US)

( * ) Notice: Subject to any disclaimer, the term of this patent is extended or adjusted under 35 U.S.C. 154(b) by 6 days.

(21) Appl. No.: 16/770,260

(22) PCT Filed: Jan. 10, 2019

(86) PCT No.: PCT/US2019/013056
§ 371 (c)(1),
(2) Date: Jun. 5, 2020

(87) PCT Pub. No.: WO2019/140093
PCT Pub. Date: Jul. 18, 2019

(65) Prior Publication Data
US 2020/0385669 A1 Dec. 10, 2020

Related U.S. Application Data

(60) Provisional application No. 62/617,414, filed on Jan. 15, 2018.

(51) Int. Cl.
*C12N 1/14* (2006.01)
*C12R 1/645* (2006.01)
*A01N 63/30* (2020.01)

(52) U.S. Cl.
CPC .............. *A01N 63/30* (2020.01); *C12N 1/14* (2013.01); *C12N 1/145* (2021.05); *C12R 2001/645* (2021.05)

(58) Field of Classification Search
CPC ................... C12N 1/14; C12R 2001/645
See application file for complete search history.

(56) References Cited

U.S. PATENT DOCUMENTS

| | | | |
|---|---|---|---|
| 4,327,181 A * | 4/1982 | Litchfield | C12N 1/38 435/911 |
| 4,332,904 A | 6/1982 | Kurane et al. | |
| 5,296,369 A | 3/1994 | Mortensen et al. | |
| 6,261,811 B1 | 6/2001 | Hamdy | |
| 7,422,737 B1 | 9/2008 | Nussinovitch et al. | |
| 2005/0266036 A1 | 12/2005 | Awada et al. | |
| 2008/0107689 A1 | 5/2008 | Seiskari | |
| 2008/0318777 A1 | 12/2008 | Lin et al. | |
| 2009/0269308 A1 | 10/2009 | Dunlap et al. | |
| 2009/0280212 A1 | 11/2009 | Sugimoto et al. | |
| 2011/0044972 A1 | 2/2011 | Fieldhouse et al. | |
| 2012/0058895 A1 | 3/2012 | Awada et al. | |
| 2012/0220464 A1 | 8/2012 | Giessler-Blank et al. | |
| 2013/0324406 A1 | 12/2013 | Chisholm et al. | |
| 2013/0337108 A1 | 12/2013 | Van Hee | |
| 2015/0037302 A1 | 2/2015 | Bralkowski et al. | |
| 2015/0044356 A1 | 2/2015 | Bootsma et al. | |
| 2015/0305347 A1 | 10/2015 | Wicks et al. | |
| 2016/0083705 A1 | 3/2016 | Milos | |
| 2016/0152525 A1 | 6/2016 | Chelle et al. | |

FOREIGN PATENT DOCUMENTS

| | | | | |
|---|---|---|---|---|
| CN | 102613252 A | 8/2012 | | |
| CN | 103468622 A | 12/2013 | | |
| CN | 105087383 A | 11/2015 | | |
| EP | 2390345 A1 | 11/2011 | | |
| WO | 8103338 A1 | 11/1981 | | |
| WO | WO-8103338 A1 * | 11/1981 | ............... | C12N 1/38 |
| WO | 9525163 A1 | 9/1995 | | |
| WO | 2010055093 A1 | 5/2010 | | |
| WO | 2015089183 A2 | 6/2015 | | |
| WO | 2017210166 A1 | 12/2017 | | |
| WO | 2018049146 A1 | 3/2018 | | |
| WO | 2018049182 A2 | 3/2018 | | |
| WO | 2018094075 A1 | 5/2018 | | |
| WO | 2018129299 A1 | 7/2018 | | |
| WO | 2019133555 A1 | 7/2019 | | |

OTHER PUBLICATIONS

Albers et al., "Selective suppression of bacterial contaminants by process conditions during lignocellulose based yeast fermentations", Biotechnol Biofuels. 2011; 4: 59. (Year: 2011).*
Reddy et al., "Polymicrobial Multi-functional Approach for Enhancement of Crop Productivity", Chilekampalli A. Reddy, Ramu S. Saravanan, in Advances in Applied Microbiology, 2013, https://www.sciencedirect.com/topics/agricultural-and-biological-sciences/inoculum (Year: 2013).*
Rossi et al., "Growth of the Ectomycorrhizal Fungus *Pisolithus microcarpus* in different nutritional conditions", Braz J Microbiol. Apr. 2011;42(2):624-32 (Year: 2011).*
Tanaka et al., "A Hidden Pitfall in the Preparation of Agar Media Undermines Microorganism Cultivability", Applied and Environmental Microbiology, Dec. 2014 vol. 80 No. 24, p. 7659-7666. (Year: 2014).*
Bangrak, P., et al., "Continuous Ethanol Production Using Immobilized Yeast Cells Entrapped in Loofa-Reinforced Alginate Carriers." Brazilian Journal of Microbiology, 2011, 42: 676-684.
Das, N., et al., "Progress in the Development of Gelling Agents for Improved Culturability of Microorganisms." Frontiers in Microbiology, 2015, 6(698):1-7.
De Brito, D., Biosurfactants from renewable raw materials, Universidade do Minho Departamento de Engenharia Biologica, Nov. 2013, pp. 1-93.

(Continued)

*Primary Examiner* — Ruth A Davis
(74) *Attorney, Agent, or Firm* — Saliwanchik, Lloyd & Eisenschenk

(57) ABSTRACT

Methods are provided for cultivating fungi for scaled-up production of microbe-based products. Specifically, cultures of fungi, such as, e.g., *Pisolithus tinctorius*, are grown by aerobic submerged fermentation in liquid medium containing a particulate anchoring carrier to increase mycelial biomass.

13 Claims, No Drawings

(56) References Cited

OTHER PUBLICATIONS

De Oliveira, M., et al., "Review: Sophorolipids A Promising Biosurfactant and it's Applications." International Journal of Advanced Biotechnology and Research, 2015, 6(2): 161-174.
Duarte, J., et al., "Effect of Immobilized Cells in Calcium Alginate Beads in Alcohol Fermentation." AMB Express, 2013, 3(31): 1-8.
Santos, D., et al., "Biosurfactants: Multifunctional Biomolecules of the 21st Century." International Journal of Molecular Sciences, 2016, 17(401): 1-31.
Sen, R., "Biosurfactants: Advances in Experimental Medicine and Biology." Landes Bioscience and Springer Science+Business Media, LLC, 2010, 672: 1-331.

* cited by examiner

LARGE-SCALE AEROBIC SUBMERGED PRODUCTION OF FUNGI

CROSS REFERENCE TO A RELATED APPLICATION

This application is a National Stage Application of international Application PCT/US2019/013056, filed Jan. 10, 2019; which claims the benefit of U.S. Provisional Application Ser. No. 62/617,414, filed Jan. 15, 2018, both of which are incorporated herein by reference in their entirety.

BACKGROUND OF THE INVENTION

Microorganisms are important for the production of a wide variety of bio-preparations that are useful in many settings, such as oil production; agriculture; remediation of soils, water and other natural resources; mining; animal feed; waste treatment and disposal; food and beverage preparation and processing; and human health.

In particular, humans exploit fungi, including yeasts and molds, for countless industrial and commercial uses. For example, fungi have been used for generations in the production of fermented foods and beverages, e.g., soy sauce, wine, beer, spirits, breads, miso, tempeh, kimchi, and cheeses are all produced through fungal fermentative processes. Additionally, many fungi are themselves edible, such as a variety of mushroom-forming species.

Fungi are also useful in biotechnology as research models and for the production of pharmaceuticals. For example, many anti-cholesterol statins, cyclosporins and steroids can be produced by fungi, as well as many antibiotics, such as penicillin (produced by *Penicillium notatum*).

Additionally, many fungi inhabit soil and the roots of trees and other plants, creating a symbiotic system wherein the fungi enhance plant survival and growth, even in distressed soils. See, e.g., Marx et al. 1977. Ectomycorrhizal fungi, such as *P. tinctorius*, for example, are important components of forest ecosystems as part of this symbiotic relationship, and have great potential to improve tree survival and growth in reforestation, as well as other agricultural, horticultural and arboreal applications.

Two principle forms of microbe cultivation exist for growing fungi: submerged (liquid fermentation) and surface cultivation (solid-state fermentation (SSF)). Both cultivation methods require a nutrient medium for the growth of the microorganisms, but they are classified based on the type of substrate used during fermentation (either a liquid or a solid substrate). The nutrient medium for both types of fermentation typically includes a carbon source, a nitrogen source, salts and other appropriate additional nutrients and microelements.

In particular, SSF utilizes solid substrates, such as bran, bagasse, and paper pulp, for culturing microorganisms. One advantage to this method is that nutrient-rich waste materials can be easily recycled as substrates. Additionally, the substrates are utilized very slowly and steadily, allowing for the same substrate to be used for lengthy fermentation periods. Hence, this technique supports controlled release of nutrients. SSF is best suited for fermentation techniques involving fungi and microorganisms that require a low moisture content; however, it cannot be used in fermentation processes involving organisms that require high water activity, such as certain bacteria.

Submerged fermentation, on the other hand, is typically better suited for those microbes that require high moisture. This method utilizes free flowing liquid substrates, such as molasses and nutrient broth, into which bioactive compounds are secreted by the growing microbes. While submerged cultivation can be achieved relatively quickly, it does possess certain drawbacks. For example, the substrates are utilized quite rapidly, thus requiring constant replenishment and/or supplementation with nutrients. Additionally, it requires more energy, more stabilization, more sterilization, more control of contaminants, and often a more complex nutrient medium than is required for SSF. Furthermore, transporting microorganisms produced by submerged cultivation can be complicated and costly, in addition to the difficulty for laborers to implement the process in the field, e.g., in a remote location where the product will be used.

Microbes, such as fungi, have the potential to play highly beneficial roles in, for example, agriculture, forestry and soil reclamation; however, one limiting factor in commercialization of microbe-based products has been the cost per propagule density, where it is particularly expensive and often unfeasible to apply microbial products to large scale operations with sufficient inoculum to see the benefits. This is, in part, due to the difficulties in cultivating efficacious microbial products on a large scale. For example, current procedures for cultivating mycorrhizal fungi on solid media are time-consuming and do not lend themselves to efficient and cost-effective large-scale production, as growth rates are slow and culture yields are low. Submerged aerobic fermentation could also be useful in mass-producing fungi. Unfortunately, however, no submerged aerobic fermentation method exists for mycelial and sporulating fungi at a low cost and without requiring stationary large-scale production facilities.

In light of the difficulties outlined above, and further in light of the widespread potential for fungi-based products in industry and commerce, methods are needed for efficient production of efficacious fungi-based products on an industrial scale.

BRIEF SUMMARY OF THE INVENTION

The present invention is directed toward the mass cultivation of microbe-based products for commercial application. In preferred embodiments, materials and methods are provided for the efficient production and use of beneficial microbes, as well as for the production and use of substances, such as metabolites, derived from these microbes and the substrate in which they are produced.

Advantageously, the subject invention can be used as a "green" process for producing microorganisms on a large scale and at low cost, without releasing harmful chemicals into the environment. Furthermore, the subject invention is operationally-friendly, and allows for the manufacture of fungi-based products in amounts sufficient to treat thousands to millions of acres of, e.g., crops and/or forests.

In one embodiment, a method is provided for cultivating microbe-based products comprising fungi and/or fungal growth by-products. The method can further be used to produce inocula for producing fungi-based products on an industrial scale. Preferably, the method utilizes submerged aerobic cultivation. Methods are also provided for using these fungi-based products.

In one embodiment, a method of cultivating fungi-based products on a commercial scale is provided, the method comprising inoculating a liquid growth medium with a fungal strain; suspending a particulate anchoring carrier in the liquid growth medium as a site for nucleating fungal growth; adding one or more antibacterial substances to the liquid growth medium; and cultivating the strain by aerobic submerged fermentation.

Preferably, the method is carried out in a portable, distributable fermentation reactor that can be operated at or near the site of application of the fungi-based product. The method and equipment for cultivation can be performed in a batch process, fed batch process or a quasi-continuous process.

In one embodiment, the method can further comprise harvesting the fungi from the reactor and, optionally, drying the fungi by freeze-drying, spray-drying or drum-drying. The dried product can be further milled if desired.

Organisms that can be cultured using the subject invention can include, for example, yeasts, fungi, bacteria, archaea, protozoa and plant cells. In preferred embodiments, the microorganisms are fungi, including strains that are typically difficult to cultivate on any scale. In an exemplary embodiment, the microorganisms are mycorrhizal and/or ectomycorrhizal fungi, such as, e.g., *Pisolithus tinctorius*.

In one embodiment, the liquid growth medium comprises components selected from sources of carbon, nitrogen, vitamins and minerals.

In one embodiment, the anchoring carrier can be any sterilized material suitable for serving as a nucleation site for fungal growth. Preferably, the material comprises a plurality of individual pieces that are about 0.5 mm to about 3 mm, or about 1 mm to about 2 mm in diameter. Fungi will attach to the carrier and accumulate thereon, producing fungal-carrier masses measuring, for example, at least 1 mm to 2 mm in diameter.

Advantageously, the use of the particulate anchoring carrier provides for increased production of mycelial biomass due to, for example, the increased surface area to which the fungi can attach and accumulate. Additionally, the accumulation of fungal biomass can lead to increases in the production of beneficial fungal growth by-products, such as biosurfactants. In one embodiment, the fungi grow in the form of a biofilm on the anchoring carrier.

The carrier can be inert, or it can carry and/or comprise additional nutrients and/or microbial inoculant. In some embodiments, the anchoring carrier comprises, for example, whole, or pieces of, seeds, nuts, beans or even pieces of chopped fruit, such as bananas.

In one embodiment, the anchoring carrier comprises sodium alginate beads. The beads can be prepared by, for example, continuously adding a solution comprising 3% aseptic sodium alginate and, optionally, nutrients and/or fungal inoculant, into a sterile 5% calcium chloride solution to form beads.

In one embodiment, the antibacterial substance is an antibiotic. Examples of antibiotics include, but are not limited to, streptomycin and oxytetracycline. Other antibacterial substances can include one or more of sophorolipids, rhamnolipids, lipopeptide biosurfactants, hops, and/or other substances known in the fermentation arts.

In one embodiment, prior to adding the fungal strain to the liquid culture medium, the components of the liquid culture medium can be sterilized. Additionally, water used for preparing the medium can be filtered to prevent contamination.

In one embodiment, sterilization can be achieved by placing the components of the liquid culture medium in water at a temperature of about 85-100° C. In one embodiment, sterilization can be achieved by dissolving the components in 3% hydrogen peroxide in a ratio of 1:3 (w/v).

In one embodiment, cultivation is carried out at a pH of about 2.0 to about 7.0, or about 3.0 to about 6.0.

In one embodiment the subject invention provides microbe-based products comprising one or more microorganisms and/or their growth by-products. The subject microbe-based products can comprise yeasts, fungi, bacteria, archaea, protozoa or plant cells. In preferred embodiments, the microorganisms are fungi.

The fungi-based products can comprise the microorganisms themselves and/or their growth by-products, as well as residual growth medium and/or anchoring carrier materials. The microorganisms can be viable or in an inactive form. They can be in the form of vegetative cells, spores, conidia, mycelia and/or a combination thereof. Preferably, they are in the form of mycelia.

Advantageously, the fungi-based products can be scaled up to industrial scale concentrations and formulated as, for example, biofertilizers and biopesticides, which can be useful in applications including, for example, commercial agriculture, gardening, horticulture, greenhouse production, forestry, and soil reclamation. Additionally, the fungi-based products can be used for, e.g., plant growth stimulation and pest suppression for a wide variety of plants and soil environments.

In one embodiment, methods for enhancing plant health and growth are provided, wherein the roots of a plant and/or the surrounding soil in which a plant grows are inoculated with a microbe-based product of the subject invention. In one embodiment, the method is carried out before, concurrently with, and/or after planting the plant in soil.

In one embodiment, the method can be used for improving and/or reclaiming the soils of strip-mined lands, and/or lands destroyed by fires, erosion, and other disasters. In one embodiment, the method can be used for restoring forests and woods after industrial deforestation. In one embodiment, the method can increase crop production while dramatically decreasing the dependence on expensive and hazardous chemical fertilizers.

DETAILED DESCRIPTION

Materials and methods are provided for cultivating fungi for scaled-up production of microbe-based products. Specifically, cultures of fungi, such as, e.g., *Pisolithus tinctorius*, are grown by aerobic submerged fermentation in liquid medium containing a particulate anchoring carrier to increase mycelial biomass.

In one embodiment, a method is provided for cultivating microbe-based products comprising fungi and/or fungal growth by-products. The method can further be used to produce inocula for producing fungi-based products on an industrial scale. Methods are also provided for using these fungi-based products.

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. The microbes can be present, with medium in which they were grown, in the microbe-based composition. The cells may be present at, for example, a concentration of $1\times10^4$, $1\times10^5$, $1\times10^6$, $1\times10^7$, $1\times10^8$, $1\times10^9$, $1\times10^{10}$, $1\times10^{11}$, $1\times10^{12}$ or $1\times10^{13}$ or more CFU per ml of the composition.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as plant hormones, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, a "biofilm" is a complex aggregate of microorganisms, wherein the cells adhere to each other and produce extracellular substances that encase the cells. Biofilms can also adhere to surfaces. The cells in biofilms are physiologically distinct from planktonic cells of the same organism, which are single cells that can float or swim in liquid medium.

As used herein, "enhancing" means improving or increasing. For example, enhanced plant health means improving the plant's ability to grow and thrive, including the plant's ability to ward off pests and/or diseases, and the plant's ability to survive droughts and/or overwatering. Enhanced plant growth means increasing the size and/or mass of a plant, or improving the ability of the plant to reach a desired size and/or mass. Enhanced yields mean improving the end products produced by the plants, for example, by increasing the number of fruits per plant, increasing the size of the fruit, and/or improving the quality of the fruit (e.g., taste, texture).

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. An "isolated" microbial strain means that the strain is removed from the environment in which it exists in nature. Thus, the isolated strain may exist as, for example, a biologically pure culture, or as spores (or other forms) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (e.g., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites include, but are not limited to, enzymes, acids, solvents, alcohols, proteins, vitamins, minerals, microelements, amino acids, polymers, and surfactants.

As used herein, "plurality" means a number greater than 1.

As used herein, "reduces" means a negative alteration of at least 1%, 5%, 10%, 25%, 50%, 75%, or 100%.

As used herein, "reference" means a standard or control condition.

As used herein, "surfactant" means a compound that lower the surface tension (or interfacial tension) between two liquids or between a liquid and a solid. Surfactants act as detergents, wetting agents, emulsifiers, foaming agents, and dispersants. A "biosurfactant" is a surface-active substance produced by a living cell.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19, or 20 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference in their entirety.

Growth of Microbes

In preferred embodiments, the subject invention provides methods for cultivating microbe-based products, using novel procedures and systems for aerobic submerged fermentation. As used herein "fermentation" refers to growth of cells under controlled conditions. The growth could be aerobic or anaerobic. In preferred embodiments, fermentation is performed aerobically.

In one embodiment, the subject invention provides materials and methods for the production of biomass (e.g., viable cellular material), extracellular metabolites (e.g. small molecules, polymers and excreted proteins), residual nutrients and/or intracellular components (e.g. enzymes and other proteins).

Specifically, in preferred embodiments, the methods can be used to produce fungi-based products comprising, for example, the ectomycorrhizal fungi, *Pisolithus tinctorius*. Other fungal strains can also be produced using the subject methods, including those that are known to be difficult to cultivate on any scale.

In one embodiment, a method of cultivating fungi-based products on a commercial scale is provided, the method comprising inoculating a liquid growth medium with a fungal strain; suspending a particulate anchoring carrier in the liquid growth medium as a site for nucleating fungal growth; adding one or more antibacterial substances to the liquid growth medium; and cultivating the strain by aerobic submerged fermentation.

In one embodiment, the anchoring carrier can be any sterilized material suitable for serving as a nucleation site for fungal growth. Preferably, the material comprises a plurality of individual pieces that are about 0.5 mm to about 3 mm, or about 1 mm to about 2 mm in diameter. Fungi will attach to the carrier and accumulate thereon, producing fungal-carrier masses measuring, for example, at least 1 mm to 2 mm in diameter.

Advantageously, the use of the particulate anchoring carrier provides for increased production of mycelial biomass due to, for example, the increased surface area to which the fungi can attach and accumulate. Additionally, the accumulation of fungal biomass can lead to increases in the production of beneficial fungal growth by-products, such as biosurfactants. In one embodiment, the fungi grow in the form of a biofilm on the anchoring carrier.

The carrier can be inert, or it can carry and/or comprise additional nutrients and/or microbial inoculant. In some embodiments, the anchoring carrier comprises, for example, whole, or pieces of, seeds, nuts, beans or even pieces of chopped fruit, such as bananas.

In one embodiment, the anchoring carrier comprises sodium alginate beads. The beads can be prepared by, for example, continuously adding drops of a solution comprising 3% aseptic sodium alginate and optional nutrients and/or fungal inoculant, into a sterile 5% calcium chloride solution to form beads.

In one embodiment, the subject method can further comprise harvesting the fungal-carrier masses that form on the anchoring carrier from the reactor and, optionally, drying them by, for example, freeze-drying, spray-drying or drum-drying. The dried product can be further milled if desired.

In some embodiments, the fungi can be separated from the anchoring carrier prior to drying. In other embodiments, the fungi remain attached to the anchoring carrier and the entire fungal-carrier mass is dried and, optionally, milled.

In one embodiment, the antibacterial substance is an antibiotic. Examples of antibiotics include, but are not limited to, streptomycin and oxytetracycline. Other antibacterial substances can include one or more of sophorolipids, rhamnolipids, lipopeptide biosurfactants, hops, and/or others known in the fermentation arts.

In one embodiment, prior to adding the fungal strain to the liquid culture medium, the components of the liquid culture medium can optionally be sterilized. Additionally, water used for preparing the medium can be filtered to prevent contamination.

In one embodiment, sterilization of the nutrient medium can be achieved by placing the components of the liquid culture medium in water at a temperature of about 85-100° C. In one embodiment, sterilization can be achieved by dissolving the components in 3% hydrogen peroxide in a ratio of 1:3 (w/v).

The microbe growth vessel used according to the subject invention can be any fermenter or cultivation reactor for industrial use. In a preferred embodiment, the reactor is part of a portable, distributed system for fermentation, which can be operated at or near the site of application of the fungi-based product. The method and equipment for cultivation can be performed in a batch process, fed batch process or a quasi-continuous process.

Advantageously, the microorganisms of interest can be cultivated on a small or large scale onsite. Similarly, the microbial metabolites can also be produced in large quantities at the site of need. Furthermore, the microbe-based products can be produced in remote locations. The microbe growth facilities may operate off the grid by utilizing, for example, solar, wind and/or hydroelectric power.

In certain embodiments, the method is carried out in a reactor with working volume of about 500-2,000 L, or about 750-850 L. However, sizes and configuration of reactors may vary (depending on the microorganism and/or growth by-products of interest).

In one embodiment, the vessel may optionally have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

In one embodiment, the liquid nutrient medium comprises a nitrogen source. The nitrogen source can be, for example, an organic or inorganic nitrogen source, such as, for example, a protein, an amino acid, potassium nitrate, yeast extract, yeast autolysates, urea, ammonia, or preferably ammonium salts, such as, ammonium nitrate ammonium sulfate, ammonium phosphate, and/or ammonium chloride. These nitrogen sources may be used independently or in a combination of two or more.

In one embodiment, the liquid nutrient medium comprises a carbon source. The carbon source is typically a carbohydrate, such as glucose, sucrose, lactose, fructose, trehalose, mannose, raffinose, mannitol, sorbose, ribose, citrate, molasses, hydrolyzed starch, corn syrup, and/or maltose; organic acids such as acetic acid, fumaric acid, citric acid, propionic acid, malic acid, malonic acid, and/or pyruvic acid; alcohols such as ethanol, propanol, butanol, xylitol, pentanol, hexanol, isobutanol, and/or glycerol; fats and oils such as soybean oil, coconut oil, canola oil, rice bran oil, olive oil, corn oil, sesame oil, and/or linseed oil; etc. These carbon sources may be used independently or in a combination of two or more. In preferred embodiments, the carbon sources are selected from glucose, mannose, galactose, sucrose, and hydrolyzed starch.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in corn steep liquor, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included in the medium. Usable inorganic salts can be potassium dihydrogen phosphate, dipotassium hydrogen phosphate, disodium hydrogen phosphate, magnesium sulfate, magnesium chloride, iron sulfate (e.g., ferrous sulfate heptahydrate), iron chloride, manganese sulfate, manganese sulfate monohydrate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may comprise adding acids and/or antibacterial substances to the medium before and/or during the cultivation process. Antibacterial substances can include antibiotics, such as, for example, streptomycin, oxytetracycline. Other antibacterial substances can include one or more of sophorolipids, rhamnolipids, lipopeptide biosurfactants and hops, among others known in the fermentation arts.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The pH of the mixture should be suitable for the microorganism of interest, though advantageously, stabilization of pH using buffers or pH regulators is not necessary when using the subject cultivation methods. Control or maintenance of pH in the course of the fermentation may be accomplished using manual or automatic techniques conventional in the art, such as using automatic pH controllers for adding base. Preferred bases employed for pH control include but are not limited to NaOH and KOH. In preferred embodiments, the optimum pH for cultivation ranges between about 2.0 to about 7.0, or about 2.5 to about 6.0, or about 3.0 to about 4.0.

In one embodiment, the method for cultivation is carried out at about 5 to about 100° C., preferably, 15 to 40° C., more preferably, 25 to 30° C. In a further embodiment, the cultivation may be carried out continuously at a constant temperature. In another embodiment, the cultivation may be subject to changing temperatures.

In one embodiment, total sterilization of equipment and substrate used in the subject cultivation methods is not necessary. However, the equipment and substrate can optionally be sterilized. The cultivation equipment such as the reactor/vessel may be separated from, but connected to, a sterilizing unit, e.g., an autoclave or steam sterilizing system. The cultivation equipment may also have a sterilizing unit that sterilizes in situ before starting the inoculation. Air can be sterilized by methods know in the art. For example, the ambient air can pass through at least one filter before being introduced into the vessel.

In one embodiment, the fermentation reactors are not sterilized using traditional methods. Instead, a method of empty vessel sanitation can be used, which comprises treating the internal surfaces of the reactor vessel with 2% to 3% hydrogen peroxide and rinsing with bleach and high pressure hot water prior to initiating cultivation.

In one embodiment, the subject methods of cultivation can be used for producing a microbial metabolite, wherein the microorganism is cultivated under conditions appropriate for growth and production of the metabolite. In certain embodiment, the methods provide for enhanced production of a metabolite compared with traditional fermentation methods.

The metabolites can include, for example, biosurfactants, biopolymers, enzymes, ethanol, lactic acid, beta-glucan, proteins, peptides, metabolic intermediates, polyunsaturated fatty acids, lipids or others as are describe herein. The metabolite content produced by the method can be, for example, at least 20%, 30%, 40%, 50%, 60%, 70%, 80%, or 90%.

In one embodiment, the metabolite is a biosurfactant. Biosurfactants according to the subject invention include, for example, low-molecular-weight glycolipids, cellobiose lipids, lipopeptides, flavolipids, phospholipids, and high-molecular-weight polymers such as lipoproteins, lipopolysaccharide-protein complexes, and/or polysaccharide-protein-fatty acid complexes.

The microbial growth by-product produced by microorganisms of interest may be retained in the microorganisms or secreted into the substrate. In another embodiment, the method for producing microbial growth by-product may further comprise steps of concentrating and purifying the microbial growth by-product of interest. In a further embodiment, the substrate may contain compounds that stabilize the activity of microbial growth by-product.

In one embodiment, all of the microbial cultivation composition is removed upon the completion of the cultivation (e.g., upon, for example, achieving a desired mycelial density, or density of a specified metabolite). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free substrate or contain cells. In this manner, a quasi-continuous system is created.

Microbial Strains Grown in Accordance with the Subject Invention

The microorganisms grown according to the systems and methods of the subject invention can be, for example, fungi, bacteria, archaea, protozoa and plant cells. These microorganisms may be natural, or genetically modified microorganisms. For example, the microorganisms may be transformed with specific genes to exhibit specific characteristics. The microorganisms may also be mutants of a desired strain.

As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microbes are fungi, including yeasts and molds. Examples of fungal species suitable for use according to the current invention, include, but are not limited to, *Acaulospora, Ascomycota, Aspergillus, Aureobasidium* (e.g., *A. pullulans*), *Basidiomycota, Blakeslea, Candida* (e.g., *C. albicans, C. apicola, C. bombicola, C. nodaensis*), *Cryptococcus, Debaryomyces* (e.g., *D. hansenii*), *Entomophthora, Fusarium, Hanseniaspora* (e.g., *H. uvarum*), *Hansenula, Issatchenkia, Kluyveromyces* (e.g., *K. phaffii*), *Leccinum, Mortierella, Mucor* (e.g., *M. piriformis*), *Mycorrhiza, Penicillium, Phythium, Phycomyces, Pichia* (e.g., *P. anomala, P. guielliermondii, P. occidentalis, P. kudriavzevii*), *Pisolithus* spp. (e.g., *P. tinctorius*), *Rhizopus, Saccharomyces* (e.g., *S. boulardii sequela, S. cerevisiae, S. torula*), *Pseudozyma* (e.g., *P. aphidis*), *Starmerella* (e.g., *S. bombicola*), *Thraustochytrium, Torulopsis, Trichoderma* (e.g., *T. reesei, T. harzianum, T. hamatum, T. viride*), *Ustilago* (e.g., *U. maydis*), *Wickerhamomyces* (e.g., *W. anomalus*), *Williopsis* (e.g., *W. mrakii*), *Zygomycota*, and *Zygosaccharomyces* (e.g., *Z. bailii*).

In an exemplary embodiment, the microorganisms are mycorrhizal fungi, including ectomycorrhizal fungi, such as *Pisolithus tinctorius* (also known as the "dyemaker's puffball" or "horse dung fungus").

There are thousands of ectomycorrhizal fungi, which belong to the taxa *Basidiomycota, Ascomycota*, and *Zygomycota*. These fungi form in symbiotic relationships with the roots of around 10% of plant families. An individual tree may have 15 or more different fungal relationships at one time.

Some ectomycorrhizal fungi, such as many *Leccinum* and *Suillus*, are symbiotic with only one particular genus of plant, while other fungi, such as the *Amanita* and *Pisolithus*, are generalists that form mycorrhizas with many different plants. Ectomycorrhiza consist of a hyphal sheath, or mantle, covering the root tip and a Hartig net of hyphae surrounding the plant cells within the root cortex. Outside the root, Ectomycorrhizal extramatrical mycelium forms an extensive network within the soil and leaf litter. The fungus gains carbon and other essential organic substances from a plant, and in return, helps the plant take up water, mineral salts and metabolites. It can also fight off parasites, nematodes and soil pathogens.

Compositions According to the Subject Invention

The subject invention provides compositions comprising one or more microorganisms and/or one or more microbial growth by-products. Preferably, the microorganisms are fungi. In an exemplary embodiment, the fungi are mycorrhizal and/or ectomycorrhizal fungi, such as, e.g., *Pisolithus tinctorius*.

The fungi-based products can comprise the microorganisms themselves and/or their growth by-products, as well as residual growth medium and/or anchoring carrier materials. The microorganisms can be viable or in an inactive form. They can be in the form of vegetative cells, spores, conidia, mycelia and/or a combination thereof. Preferably, they are in the form of mycelia.

Mycelia are the vegetative propagules of a fungus, consisting of a mass of branching, thread-like hyphae that facilitate attachment to plant roots. Mycelia can be produced using both solid and liquid medium fermentation methods. Furthermore, mycelia-based products, under appropriate production and storage conditions, can retain viability for 6-9 months.

Advantageously, the fungi-based products can be scaled up to industrial scale concentrations and formulated as, for example, biofertilizers and biopesticides, which can be useful in applications including, for example, commercial agriculture, gardening, horticulture, greenhouse production, forestry, and soil reclamation. Additionally, the fungi-based products can be used for, e.g., plant growth stimulation and pest suppression for a wide variety of plants and soil environments.

Methods of Use

The compositions of the subject invention can be used for a variety of purposes. In certain embodiments, methods are provided for enhancing plant health and growth, wherein the subject compositions are applied to the plant and/or its surrounding environment.

The methods can further comprise adding materials to enhance microbe growth during application (e.g., adding nutrients to promote microbial growth). In one embodiment, the nutrient sources can include, for example, sources of nitrogen, potassium, phosphorus, magnesium and/or carbon.

In one embodiment, methods for enhancing plant health and growth are provided, wherein the fungi-based product is applied to the plant and/or its surrounding environment.

As used herein, "applying" a composition or product, or "treating" an environment refers to contacting a composition or product with a target or site such that the composition or product can have an effect on that target or site. The effect can be due to, for example, microbial growth and/or the action of a metabolite, enzyme, biosurfactant or other growth by-product.

In some embodiments, the microbe-based product is applied directly to a plant, plant part, and/or the plant's surrounding environment (e.g., the soil). The fungi-based product can be applied as a seed treatment or coating, a root treatment or to the soil surface. It can be, for example, sprayed or poured as a liquid or a dry powder, or as freeze-dried cells, or as granules, pellets, gels or pastes.

The soils can also be treated with liquid or dry formulations of the products, for example, through the irrigation system as a liquid solution. The product can be mixed into the soil via, for example, tilling.

In one embodiment, the use of nucleating carriers to produce the fungi-based compositions helps to improve application of the product because the masses comprising fungi and carrier can easily be harvested and dried as one product. If the product is used in dried form, water or other liquids will activate the dried cells. Other activators can be added to the product if desired, such as, for example, L-alanine or manganese.

Plants and/or their environments can be treated at any point during the process of cultivating the plant. For example, the fungi-based product can be applied to the soil prior to, concurrently with, or after the time when seeds and/or plants are planted therein. It can also be applied at any point thereafter during the development and growth of the plant, including when the plant is flowering, fruiting, and during and/or after abscission of leaves.

In one embodiment, the method can be used for improving and/or reclaiming the soils of strip-mined lands, and/or lands destroyed by fires, erosion, and other disasters. In one embodiment, the method can be used for restoring forests and woods after industrial deforestation. In one embodiment, the method can increase crop production while dramatically decreasing the dependence on expensive and harsh chemical fertilizers.

Both the liquid and dry cultures can be used in the areas of reforestation, for improving growth of various trees and bushes and for improving the yield of horticultural, ornamental, steppe and prairie plants, as well as plants in a variety of other vegetative environments.

In one embodiment, the composition can be used in agriculture. For example, methods are provided wherein the composition is applied to a plant and/or its environment to treat and/or prevent the spread of pests and/or diseases. The composition can also be useful for enhancing water dispersal and absorption in the soil, as well as enhancing nutrient absorption from the soil through plant roots.

Other uses for the subject compositions include, but are not limited to, biofertilizers, biopesticides, bioleaching, bioremediation of soil and water, control of unwanted microbial growth, and many others.

Target Plants

As used here, the term "plant" includes, but is not limited to, any species of woody, ornamental or decorative, crop or cereal, fruit plant or vegetable plant, flower or tree, macroalga or microalga, phytoplankton and photosynthetic algae (e.g., green algae *Chlamydomonas reinhardtii*). "Plant" also includes a unicellular plant (e.g. microalga) and a plurality of plant cells that are largely differentiated into a colony (e.g. volvox) or a structure that is present at any stage of a plant's development. Such structures include, but are not limited to, a fruit, a seed, a shoot, a stem, a leaf, a root, a flower petal, etc. Plants can be standing alone, for example, in a garden, or can be one of many plants, for example, as part of an orchard, crop or pasture.

Example of plants for which the subject invention is useful include, but are not limited to, cereals and grasses (e.g., wheat, barley, rye, oats, rice, maize, *sorghum*, corn), beets (e.g., sugar or fodder beets); fruit (e.g., grapes, strawberries, raspberries, blackberries, pomaceous fruit, stone fruit, soft fruit, apples, pears, plums, peaches, almonds, cherries or berries); leguminous crops (e.g., beans, lentils, peas or soya); oil crops (e.g., oilseed rape, mustard, poppies, olives, sunflowers, coconut, castor, cocoa or ground nuts); cucurbits (e.g., pumpkins, cucumbers, squash or melons); fiber plants (e.g., cotton, flax, hemp or jute); citrus fruit (e.g., oranges, lemons, grapefruit or tangerines); vegetables (e.g., spinach, lettuce, asparagus, cabbages, carrots, onions, tomatoes, potatoes or bell peppers); Lauraceae (e.g., avocado, Cinnamonium or camphor); and also tobacco, nuts, herbs, spices, medicinal plants, coffee, eggplants, sugarcane, tea, pepper, grapevines, hops, the plantain family, latex plants, cut flowers and ornamentals.

Types of plants that can benefit from application of the products and methods of the subject invention include, but are not limited to: row crops (e.g., corn, soy, *sorghum*, peanuts, potatoes, etc.), field crops (e.g., alfalfa, wheat, grains, etc.), tree crops (e.g., walnuts, almonds, pecans, hazelnuts, pistachios, etc.), citrus crops (e.g., orange, lemon, grapefruit, etc.), fruit crops (e.g., apples, pears, strawberries, blueberries, blackberries, etc.), turf crops (e.g., sod), ornamentals crops (e.g., flowers, vines, etc.), vegetables (e.g., tomatoes, carrots, etc.), vine crops (e.g., grapes, etc.), forestry (e.g., pine, spruce, eucalyptus, poplar, etc.), managed pastures (any mix of plants used to support grazing animals).

Further plants that can benefit from the products and methods of the invention include all plants that belong to the superfamily Viridiplantae, in particular monocotyledonous and dicotyledonous plants including fodder or forage legumes, ornamental plants, food crops, trees or shrubs selected from *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp., *Artocarpus* spp., *Asparagus officinalis, Avena* spp. (e.g., *A. sativa, A. fatua, A. byzantina, A. fatua* var. *sativa, A. hybrida*), *Averrhoa carambola, Bambusa* sp., *Benincasa hispida, Bertholletia excelsea, Beta vulgaris, Brassica* spp. (e.g., *B. napus, B. rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba penlandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g., *E. guineensis, E. oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g., *G. max, Soja hispida* or *Soja max*), *Gossypium hirsutum, Helianthus* spp. (e.g., *H. annuus*), *Hemerocallis fulva, Hibiscus* spp., *Hordeum* spp. (e.g., *H. vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g., *L. esculentum, L. lycopersicum, L. pyriforme*), *Macrotyloma* spp., *Malus* spp., *Malpighia emarginata, Mammea americana, Mangifera indica, Manihot* spp., *Manilkara zapota, Medicago saliva, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g., *O. sativa, O. latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g., *S. tuberosum, S. integrifolium* or *S. lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g., *T. aestivwn, T. durum, T. turgidum, T. hybernum, T. macho, T. sativum, T. monococcum* or *T. vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

Further examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tincto-* rius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, *sorghum*, wheat, millet, tobacco, etc.), such as corn and soybean plants.

Turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerate*); perennial ryegrass (*Lolium perenne*); red fescue (*Festuca rubra*); redtop (*Agrostis alba*); rough bluegrass (*Poa trivialis*); sheep fescue (*Festuca ovine*); smooth bromegrass (*Bromus inermis*); tall fescue (*Festuca arundinacea*); timothy (*Phleum pretense*); velvet bentgrass (*Agrostis canine*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, *sorghum*, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mungbean, lima bean, fava bean, lentils, chickpea, etc.

Further plants of interest include *Cannabis* (e.g., sativa, indica, and ruderalis) and industrial hemp.

All plants and plant parts can be treated in accordance with the invention. In this context, plants are understood as meaning all plants and plant populations such as desired and undesired wild plants or crop plants (including naturally occurring crop plants). Crop plants can be plants that can be obtained by traditional breeding and optimization methods or by biotechnological and recombinant methods, or combinations of these methods, including the transgenic plants and the plant varieties.

Plant parts are understood as meaning all aerial and subterranean parts and organs of the plants such as shoot, leaf, flower and root, examples which may be mentioned being leaves, needles, stalks, stems, flowers, fruit bodies, fruits and seeds, but also roots, tubers and rhizomes. The plant parts also include crop material and vegetative and generative propagation material, for example cuttings, tubers, rhizomes, slips and seeds.

Preparation of Fungi-Based Products

One microbe-based product of the subject invention is simply the substrate containing the microorganism and/or the microbial metabolites produced by the microorganism and/or any residual nutrients. Upon harvesting of the solid substrate, microbe, and/or by-products, the product can be easily dried (e.g., freeze- or spray-dried) and optionally, dissolved in water (e.g., in a storage tank). The product of fermentation may be used directly without extraction or purification. If desired, extraction and purification can be easily achieved using standard extraction and/or purification methods or techniques known to those skilled in the art.

The microorganisms in the fungi-based product may be in an active or inactive form. Preferably, the microorganisms are in mycelial form. The microbe-based products may be used without further stabilization, preservation, and storage. Advantageously, direct usage of these fungi-based products preserves a high viability of the microorganisms, reduces the possibility of contamination from foreign agents and undesirable microorganisms, and maintains the activity of the by-products of microbial growth.

The microbes and/or liquid containing the culture can be removed from the storage tank and transferred to the site of application via, for example, tanker for immediate use.

In other embodiments, the composition (in the form of dried or dissolved liquid form) can be placed in containers of appropriate size, taking into consideration, for example, the intended use, the contemplated method of application, the size of the fermentation vessel, and any mode of transportation from microbe growth facility to the location of use. Thus, the containers into which the microbe-based composition is placed may be, for example, from 1 gallon to 1,000 gallons or more. In certain embodiments the containers are 2 gallons, 5 gallons, 25 gallons, or larger.

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, pesticides, and other ingredients specific for an intended use.

Advantageously, in accordance with the subject invention, the mycorrhizal fungi-based product may comprise the substrate in which the microbes were grown. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., a citrus grove). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. This allows for a scaled-down bioreactor (e.g., smaller fermentation vessel, smaller supplies of starter material, nutrients and pH control agents), which makes the system efficient and can eliminate the need to stabilize cells or separate them from their culture medium. Local generation of the microbe-based product also facilitates the inclusion of the growth medium in the product, when desired. The medium can contain agents produced during the fermentation that are particularly well-suited for local use.

Locally-produced high density, robust cultures of microbes are more effective in the field than those that have remained in the supply chain for some time. The microbe-based products of the subject invention are particularly advantageous compared to traditional products wherein cells have been separated from metabolites present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells or propagules, or a mixture of vegetative cells and propagules.

In one embodiment, the microbe growth facility is located on, or near, a site where the microbe-based products will be used (e.g., a citrus grove), for example, within 300 miles, 200 miles, or even within 100 miles. Advantageously, this allows for the compositions to be tailored for use at a specified location. The formula and potency of microbe-based compositions can be customized for specific local conditions at the time of application, such as, for example, which soil type, plant and/or crop is being treated; what season, climate and/or time of year it is when a composition is being applied; and what mode and/or rate of application is being utilized.

Advantageously, distributed microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated medium and metabolites in which the cells are originally grown.

Furthermore, by producing a composition locally, the formulation and potency can be adjusted in real time to a specific location and the conditions present at the time of application. This provides advantages over compositions that are pre-made in a central location and have, for example, set ratios and formulations that may not be optimal for a given location.

The microbe growth facilities provide manufacturing versatility by their ability to tailor the microbe-based products to improve synergies with destination geographies. Advantageously, in preferred embodiments, the systems of the subject invention harness the power of naturally-occurring local microorganisms and their metabolic by-products to improve plant health, root growth and productivity.

The cultivation time for the individual vessels may be, for example, from 1 to 7 days or longer. The cultivation product can be harvested in any of a number of different ways.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Preparation of *P. tinctorius* Inoculum Using Solid Medium

To obtain starter cells for liquid culture and to compare the growth rate on solid culture, mycelia of *P. tinctorius* were inoculated into petri dishes containing solid MPG agar. The MPG nutrient medium comprised (g/l): peptone (10.0) yeast extract (2.0), dextrose (30.0), agar (20.0), $KH_2PO_4$ (2.38), $K_2PO_4$ (5.65), $MgSO_4$ (1.00), $NH_4NO_3$ (3.0), $CuSO_4$ (0.0064), $FeSO_4$ (0.0011), $MnCl_2$ (0.0019), $ZnSO_4$ (0.0015). The pH was kept at 5.0-6.0. The inoculated plates were incubated at 30° C. for 5 to 10 days.

To expedite the growth of mycelia, 10 ppm of malic acid (pH 4.0) can be added to the solid medium.

Example 2—Preparation of *P. tinctorius* Inoculum Using Liquid Culture

The liquid growth medium used for preparing fungal inocula was obtained by omitting agar from the MPG nutrient medium of Example 1. Mycelia produced in Example 1 were then used to inoculate the agar-less MPG solution. Five 4 L flasks with 1 liter of culture were seeded and grown in a shaker. The fungus was incubated at 30° C. for 5-7 days.

Growth rates of *P. tinctorius* were essentially equal at pH levels ranging from 4.0 to 6.0. The addition of an anchoring carrier to the liquid medium in the flasks improved growth rate in all cases.

Example 3—Liquid Culture Production in a Portable Bioreactor

A portable reactor was used to produce large-scale quantities of *P. tinctorius* culture. The working volume of the reactor was between 750 to 850 L. The reactor was filled with water. PGK medium was prepared, comprising (g/L): glucose (10.0); peptone (3.33); yeast extract (0.67); $NH_4NO_3$ (1.0); $KH_2PO_4$ (0.264); $K_2HPO_4$ (0.628); $MgSO_4$ (0.33); $CuSO_4$ (0.0021); $MnCl_2$ (0.0006); $ZnSO_4$ (0.0005); and $FeSO_4$ (0.0004). Medium components and sodium alginate beads (up to 5 g/L) were added to the reactor.

pH was measured and adjusted to the range of 4.5-5.0 using 20% phosphoric acid. The reactor was then inoculated with *Pisolithus tinctorius*, and the fungus was cultivated for 90 to 150 hours.

It should be understood that the examples and embodiments described herein are for illustrative purposes only and that various modifications or changes in light thereof will be suggested to persons skilled in the art and are to be included within the spirit and purview of this application.

REFERENCES

Marx, D. H., W. C. Bryan, C. E. Cordell. (1977). *Survival and Growth of Pine Seedlings with Pisolithus Ectomycorrhizae after Two Years on Reforestation Sites in North Carolina and Florida*. Forest Science, 23:3, 363-373. https://doi.org/10.1093/forestscience/23.3.363. (Marx et al. 1977).

We claim:

1. A method of mass-producing a fungal strain and/or a fungal growth by-product, the method comprising:
   inoculating a liquid growth medium with the fungal strain;
   suspending a particulate anchoring carrier in the liquid growth medium as a site for nucleating fungal growth;
   adding one or more antibacterial substances to the liquid growth medium; and
   cultivating the strain by aerobic submerged fermentation in a reactor,
   wherein the fungal strain attaches to the anchoring carrier and accumulates thereon to form a fungal-carrier mass with diameter of at least 1 mm; wherein the components of the liquid growth medium are sterilized prior to inoculation; and wherein said sterilization comprises mixing the components with 3% hydrogen peroxide in a ratio of 1:3 (w/v).

2. The method of claim 1, wherein the anchoring carrier comprises whole, or pieces of, seeds, nuts, beans, or fruits.

3. The method of claim 1, wherein the anchoring carrier comprises alginate beads.

4. The method of claim 3, wherein the alginate beads are prepared by dropping a solution comprising 3% sodium alginate solution, and, optionally, nutrients and/or fungal inoculant, into a sterile 5% calcium chloride solution.

5. The method of claim 1, wherein the fungal-carrier mass is harvested from the reactor and, dried to produce a dry fungi-based product.

6. The method of claim 5, wherein the dry fungi-based product is milled.

7. The method of claim 5, wherein the fungal strain is separated from the carrier prior to drying.

8. The method of claim 1, wherein the fungal strain is a strain of ectomycorrhizal fungi.

9. The method of claim 8, wherein the fungal strain is a strain of *Pisolithus tinctorius*.

10. The method of claim 1, wherein the one or more antibacterial substances include streptomycin and/or oxytetracycline.

11. The method of claim 1, wherein the one or more antibacterial substances include a sophorolipid, a rhamnolipid, a lipopeptide, and/or hops.

12. The method of claim 1, carried out at a pH of about 2.0 to about 7.0.

13. The method of claim 1, wherein the fungal growth by-product is a biosurfactant.

* * * * *